US00PP18031P2

(12) United States Plant Patent
Zary

(10) Patent No.: US PP18,031 P2
(45) Date of Patent: Sep. 18, 2007

(54) HYBRID TEA ROSE PLANT NAMED 'JACHONEW'

(50) Latin Name: *Rosa hybrida*
Varietal Denomination: JAChonew

(75) Inventor: Keith W. Zary, Agoura Hills, CA (US)

(73) Assignee: Jackson and Perkins Wholesale, Inc., Medford, OR (US)

( * ) Notice: Subject to any disclaimer, the term of this patent is extended or adjusted under 35 U.S.C. 154(b) by 344 days.

(21) Appl. No.: 11/139,224

(22) Filed: May 27, 2005

(51) Int. Cl.
*A01H 5/00* (2006.01)

(52) U.S. Cl. ..... Plt./138

(58) Field of Classification Search ..... Plt./137, Plt./138

See application file for complete search history.

*Primary Examiner*—Kent Bell
*Assistant Examiner*—June Hwu
(74) *Attorney, Agent, or Firm*—Klarquist Sparkman LLP

(57) ABSTRACT

Hybrid tea rose plant having long, well formed, high centered, pink flowers; very strong flower fragrance; vigorous, upright, well branched growth; dark green, glossy, disease resistant foliage; and easily propagated on its own roots.

1 Drawing Sheet

Genus and species: *Rosa hybrida.*
Variety denomination: 'JAChonew'.

ORIGIN OF THE INVENTION

The present invention relates to a new and distinct variety of a hybrid tea rose plant named 'JAChonew' which was originated by me by crossing an unnamed, unpatented pink hybrid seedling, ('JAColite' (U.S. Plant Pat. No. 4,167)× 'KORlingo' (U.S. Plant Pat. No. 5,846)) with the variety 'MACgenev' (U.S. Plant Pat. No. 8,279).

BACKGROUND OF THE INVENTION

The primary objective of this breeding was to produce a new rose variety having the upright, well branched habit and high centered flower form of the female parent combined with the strong fragrance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Long, well formed, high centered flowers.
2. Very strong flower fragrance.
3. Vigorous, upright, well branched growth.
4. Dark green, glossy, disease resistant foliage.
5. Ease of propagation on its own roots.

Asexual reproduction of this new variety by cuttings, as performed at Somis, Calif., shows that the foregoing and all other characteristics and distinctions come true to form and are established and transmitted through succeeding propagations.

Comparison with Parents

'JAChonew' differs from the female parent as it has a much stronger fragrance and differs from the male parent in having better shaped flowers, greater resistance to mildew and having longer stems.

Comparison with Similar Variety

The closest variety is 'MACgenev' (U.S. Plant Pat. No. 8,279), the male parent.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—Unnamed pink hybrid tea seedling (not patented) ('JAColite' (U.S. Plant Pat. No. 4,167)× 'KORlingo' (U.S. Plant Pat. No. 5,846)).

*Pollen parent.*—'MACgenev' (U.S. Plant Pat. No. 8,279).

FLOWER

Observations made from January 2003 to August 2004 from plants commencing at three years of age grown in a garden environment at Somis, Calif.

Blooming habit: Continuous.
Bud:
*Size.*—About 40–45 mm long and 30–35 mm in diameter when the petals start to unfurl.
*Form.*—The bud form is very long, pointed ovoid.
*Color.*—When sepals first divide, bud color is Red Group 52B. When half blown, the upper sides of the petals are Red Group 52D with Red Group 52C on margins; and the lower sides of the petals are Red Group 55D with Red Group 54B on margins.
*Sepals.*—Color: Upper surface: Mostly Greyed-Red Group 182A with Green Group 138D on margins. Lower surface: Green Group 137B. Length: 35–50 mm. Width: 8–10 mm. Shape: Subulate. Surface texture: Upper surface: Canescent. Lower surface: Glandular. There are three heavily appendaged sepals. There are two unappendaged sepals with hairy and glandular edges.
*Receptacle.*—Color: Green Group 143C. Shape: Funnel. Size: Small, slender, about 8–10 mm long×6–8 mm wide. Surface: Hairy.
*Peduncle.*—Length: Long, averaging about 8–12 cm. Surface: Prickly, glandular. Color: Green Group 143C. Strength: Stiff, erect.
Bloom:
*Size.*—Large. Average open diameter is about 10–15 cm.
*Borne.*—Singly.
*Stems.*—Strength: Strong. Average length is about 40–60 cm with a diameter of 4–5 mm.
*Form.*—When first open: High centered. Permanence: All petals curl.
*Petalage.*—Number of petals under normal conditions: 30–35.
*Color.*—The upper sides of the petals are Red Group 52D with Red Group 52C on margins. The reverse sides of the petals are Red Group 55D with Red Group 54B on margins. The base of each petal is Yellow Group 10C. The major color on the upper side is Red Group 52D.
*Variegations.*—None.
*Discoloration.*—The general tonality at the end of the first day: Red Group 52D. At the end of the third day: Red Group 52D. Further aging: Fades to Red Group 55D before dropping on day 7–8.
*Fragrance.*—Strong, spicy damask.
Petals:
*Texture.*—Thick, coriaceous.
*Shape.*—Obovate.
*Surface.*—Smooth.
*Margin.*—Entire. Apex Shape: Obtuse. Base Shape: Rounded.
*Form.*—Moderately quilled.
*Arrangement.*—Imbricated.
*Petaloids.*—Number: 1 or 2. Color: Red Group 52D.
*Persistence.*—Petals drop off cleanly before drying.
*Lastingness.*—On the plant: Long (about 7–8 days). As a cut flower: Long (about 9–10 days).
Reproductive parts:
*Stamens.*—Number: 80–90. Length: 10–12 mm. Anthers: Length: 2–3 mm. Color: Yellow-Orange Group 20C. Arrangement: Regular around styles. Filaments: Color: Red Group 47D. Length: 7–9 mm. Pollen: Color: Yellow-Orange Group 22C.
*Pistils.*—Number: 40–45. Length: 5–6 mm. Styles: Color: Red Group 53D. Length: 4–5 mm. Stigmas: Color: Green-White Group 157D. Length: 1 mm.
*Hips.*—None observed.

PLANT

Form: Bush.
Growth: Very vigorous, upright, branching.
Age at maturity: Two years.
Mature plant: Height: 150 cm. Width: 100 cm.
Rootstock: Own roots.
Foliage: Number of leaflets on normal mid-stem leaves: 5.
*Size.*—Large. About 120 mm long×90 mm wide.
*Quantity.*—Normal.
*Color.*—New foliage: Upper side: Greyed-Purple Group 183A. Lower side: Greyed-Purple Group 183A. Old foliage: Upper side: Green Group 139A. Lower side: Green Group 139B.
Leaflets:
*Size.*—About 60 mm long×30 mm wide.
*Shape.*—Pointed oval.
*Base shape.*—Oblique.
*Apex shape.*—Acuminate.
*Texture.*—Leathery, glossy.
*Edge.*—Serrated.
*Serrations.*—Single.
*Petiole.*—Color: Green Group 139B.
*Petiole rachis.*—Color: Green Group 139B. Underside: Rough with prickles.
*Auricles.*—None.
*Stipules.*—Length: 9–11 mm smooth with a few glands.
*Color.*—Green Group 139B.
*Disease resistance.*—Resistant to rust and powdery mildew and susceptible to blackspot under normal growing conditions.
*Pest resistance.*—Not observed.
*Vein color.*—Color Group 139B.
*Venation pattern.*—Reticulate.
Wood:
*New wood.*—Color: Greyed-Purple Group 183A. Bark: Smooth.
*Old wood.*—Color: Green Group 143C. Bark: Smooth.
Prickles:
*Quantity.*—On main canes from base: 6–8 per 15 cm of stem. On laterals from main canes: 8–10 per 15 cm of stem.
*Form.*—Straight.
*Length.*—7–9 mm.
*Color when young.*—Greyed-Red Group 181A.
*Color when mature.*—Greyed-Yellow Group 161C.
Small prickles:
*Quantity.*—On main stalks: None. On laterals: Few (1 per 15 cm stem).
Winter hardiness: Hardy to Zone 5.

I claim:

1. A new and distinct variety of rose plant of the hybrid tea class, substantially as herein shown and described, characterized particularly by long, well formed, high centered, pink flowers; very strong flower fragrance; vigorous, upright, well branched growth; dark green, glossy, disease resistant foliage; and ease of propagation on its own roots.

* * * * *

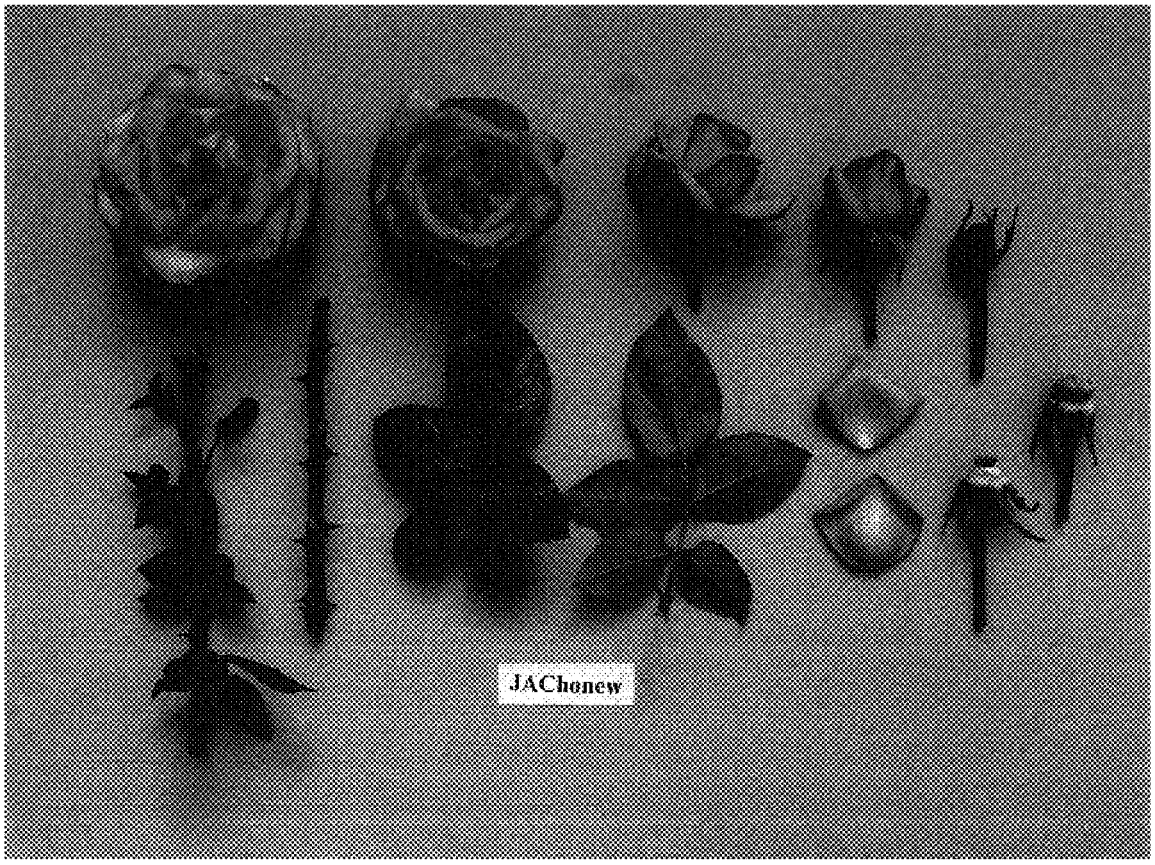
JAChonew